US009446411B2

(12) United States Patent
Manian et al.

(10) Patent No.: US 9,446,411 B2
(45) Date of Patent: Sep. 20, 2016

(54) SAMPLE ASSEMBLY FOR A MEASUREMENT DEVICE

(71) Applicant: Reametrix, Inc., San Carlos, CA (US)

(72) Inventors: Bala S. Manian, Los Altos Hills, CA (US); Pramod Kummaya, Karnataka (IN)

(73) Assignee: REAMETRIX, INC., San Carlos, CA (US)

( * ) Notice: Subject to any disclaimer, the term of this patent is extended or adjusted under 35 U.S.C. 154(b) by 18 days.

(21) Appl. No.: 13/958,076

(22) Filed: Aug. 2, 2013

(65) Prior Publication Data

US 2013/0315802 A1 Nov. 28, 2013

Related U.S. Application Data

(63) Continuation-in-part of application No. 13/034,476, filed on Feb. 24, 2011.

(51) Int. Cl.

| | |
|---|---|
| ***G01N 21/00*** | (2006.01) |
| ***C12Q 1/68*** | (2006.01) |
| ***G01N 15/06*** | (2006.01) |
| ***B01L 9/00*** | (2006.01) |
| ***B01L 3/00*** | (2006.01) |

(52) U.S. Cl.

CPC ................ *B01L 9/52* (2013.01); *B01L 3/5027* (2013.01); *B01L 9/527* (2013.01); *B01L 2200/027* (2013.01); *B01L 2200/028* (2013.01); *B01L 2200/148* (2013.01); *B01L 2300/0803* (2013.01); *B01L 2300/0816* (2013.01); *B01L 2400/0409* (2013.01)

(58) Field of Classification Search

CPC .................. G01N 21/6452; G01N 27/44721; G01N 2021/6463; G01N 21/6428; B01L 2200/028; B01L 3/5027; B01L 9/527; B01L 9/52; G01J 3/10; G01J 3/14; G01J 3/36; G01J 3/4406; G02B 21/0076; G02B 26/10

USPC ............ 422/50, 63, 68.1, 82.07, 82.08, 401, 422/554, 561

See application file for complete search history.

(56) References Cited

U.S. PATENT DOCUMENTS 4,447,395 A * 5/1984 Englar ................ G01N 33/487 422/547
5,213,764 A * 5/1993 Kerr ................ G01N 35/00029 422/511

(Continued)

FOREIGN PATENT DOCUMENTS

EP 0252632 A2 1/1988
EP 0290018 A2 11/1988

(Continued)

*Primary Examiner* — Dean Kwak
(74) *Attorney, Agent, or Firm* — Thomas Schneck

(57) ABSTRACT

A sample presentation apparatus comprises a round support movable in an optical assembly and having a flange region and an elevated gear shaped region having indexing gear cogs at intermediate radius locations of the support; a sample carrier slide holder removably supported on and movable with the support, the slide holder having at least one arm extending radially from a central hub of the sample carrier slide holder and being aligned between a first pair of indexing gear cogs; and at least one sample carrier slide removably supported on the support and aligned by the first pair of indexing gear cogs. In another embodiment of the invention, a self-aligning movable platform and support apparatus in an optical assembly comprises coarse and fine alignment mechanisms.

8 Claims, 7 Drawing Sheets

(56) References Cited

U.S. PATENT DOCUMENTS

| | | | | |
|---|---|---|---|---|
| 5,250,262 | A * | 10/1993 | Heidt et al. | 422/64 |
| 6,335,166 | B1 * | 1/2002 | Ammann | B01F 9/0001 435/6.11 |
| 6,436,349 | B1 * | 8/2002 | Carey | B01L 3/508 366/214 |
| 6,827,901 | B2 | 12/2004 | Copeland et al. | |
| 7,423,750 | B2 | 9/2008 | Hoshizaki et al. | |

FOREIGN PATENT DOCUMENTS

| | | | |
|---|---|---|---|
| EP | 0353589 | A2 | 2/1990 |
| EP | 0353590 | A2 | 7/1990 |
| EP | 0353591 | A2 | 7/1990 |
| EP | 0353592 | A2 | 7/1990 |
| JP | 8005345 | A | 1/1996 |
| JP | 9138235 | A | 5/1997 |
| JP | 11304699 | A | 11/1999 |
| JP | 2000304688 | A | 11/2000 |
| JP | 2001228088 | A | 8/2001 |
| JP | 2009074934 | A | 4/2009 |
| WO | WO9310454 | A1 | 5/1993 |
| WO | WO9419684 | A1 | 9/1994 |
| WO | WO9429024 | A1 | 12/1994 |
| WO | WO9800236 | A1 | 1/1998 |
| WO | WO2009049171 | A2 | 4/2009 |

* cited by examiner

SAMPLE ASSEMBLY FOR A MEASUREMENT DEVICE

CROSS-REFERENCE TO RELATED APPLICATION

This application is a continuation-in-part application Ser. No. 13/034,476, filed Feb. 24, 2011, which is hereby incorporated by reference.

TECHNICAL FIELD

The invention relates generally to a sample assembly for a measurement device and more specifically to a sample presentation apparatus that is versatile and may be fabricated from inexpensive methods.

BACKGROUND OF THE INVENTION

Optical detection and measurement devices are a popular choice for many different applications. They provide the advantage of speed and accuracy of results for small sample volumes. However, the use of such devices requires carefully fabricated parts that have well-known dimensions within narrow tolerance ranges. Any deviations from these ranges will lead to erroneous results, inaccurate measurements, and sometimes even complete breakdown of the device.

JP 8005345(A) illustrates an inexpensive inspection device which can be assembled with a substrate rotation table, where a plurality of printed circuit boards are fixed; and a laser application light reception. By combining the rotation of the substrate rotation table and the movement of the laser application reception part, the laser beams are applied to the entire surface of a plurality of printed circuit boards, thus obtaining height/brightness data. However, such a device is capable of being used in limited situations only.

A sample analyzer capable of analyzing light at different wavelength bands using one analyzer is elucidated in JP 2009074934(A). It comprises a first movable stage where the sample is placed and which is capable of moving the sample in width and depth, a light source which might be X-ray, ultraviolet, visible or infrared in nature; a detector for detecting transmission light or fluorescence; a second movable stage capable of moving the detector in width and depth direction. A similar invention is perceived in JP 11304699 (A) in order to obtain a near infrared component analyzer which can simultaneously analyze a plurality of kinds of samples in parallel. JP 2000304688(A) describes a simple method to measure a specimen by a simple method of moving a detection region by a detector relative to a substrate and forming a circular track of the detection region on a measurement surface. In JP 2001228088(A), the specimen chip on which a large number of living body specimens are arranged, is scanned by light to specify living body specimens labeled with a fluorescent substance. The wavelength of the scanning light corresponds to the fluorescence of the fluorescent substance from a light source and the light, is condensed by an object lens to become a prescribed spot diameter. The reflected light and fluorescence from the specimen chip are detected by a light detection member to output an electric signal. The specimen chip, rotated while moving rectilinearly is spirally scanned by the light to detect the living body specimens, to which the fluorescent substance is bonded. But, the methods and devices described herein require samples made available in carefully fabricated parts only.

WO 9800236(A1) discloses an injection molded single piece, well container suitable for reagents for use in a clinical instrument such as a protein analyzer, normally molded from a high density polyethylene or other recyclable plastic. While this piece is inexpensive, its use is limited to single kind of analysis only, and is not adaptable to other kinds of analysis.

EP 0252632(A2) describes a reagent cartridge which is used in an automated clinical analyzer; wherein the reagent cartridge is adapted to be inserted into slots formed in a reagent cartridge storage apparatus on the automated analyzer, the reagent cartridge and slots together forming a positioning and detent mechanism which removably secures the cartridge in the slot for sure and definite positioning of the cartridge during automatic operation of the analyzer. Similarly, EP 0290018(A2) discloses an automatic analyzer with multiple dose reagent pack with a plurality of vial-receiving wells and corresponding carousel containing a plurality of radially spaced compartments. EP 0353589 (A2), EP 0353590 (A2), EP 0353591(A2) and EP 0353592 (A2) and WO 9310454(A1) discloses a semi-automated biological sample analyzer consisting a carousel holding a plurality of reaction cartridges; each reaction cartridge includes a plurality of isolated test sites formed in a two dimensional array in a solid phase binding layer contained within a reaction well which is adapted to contain a biological sample to be assayed. An optical reader operating on a principle of diffuse reflectance is provided to read the results of the assays from each test site of each cartridge. Also provided is a subsystem which provides predetermined lot-specific assay calibration data which is useful for normalizing the results of various assays with respect to predetermined common standard values. Thus, a plurality of enzyme immuno assays for human IgE class antibodies specific to a panel of preselected allergens in each of a plurality of biological samples can be performed. JP 9138235(A) describes an automatic analyzer in which a cell can be measured without being removed from a cell holder; wherein the analyzer comprises a lid which can be opened and shut and installed at a cell holder so as to cover its surface part. A cell is mounted on, and attached to, the holder, claws are hooked to the other end of the cell holder, and the lid is put on the surface of the cell holder. A shock absorbing material which is installed at the cell bottom support part of the cell holder reduces the damage of the cell due to the chock to the bottom face inside the cell of the probe. The cartridges and sample containers described herein are generally expensive, or else, they are not conducive for optical measurements, but more suited for other types of measurements, such as electrical.

WO 2009049171(A2) describes a system for conducting the identification and quantification of micro-organisms, e.g., bacteria in urine samples wherein disposable cartridges are used with their components including the optical cups or cuvettes are used in the sample processor, and the optical cups or cuvettes containing the processed urine samples are used in the optical analyzer for identifying and quantifying the type of micro-organism existing in the processed urine samples. WO 9419684(A1) discloses a method and clinical system for providing immediate analytical results for biological sera of interest, such as blood-gas analysis, at the point-of-care of a patient combines a single use disposable cartridge adapted to interface with an associated portable electroanalytical instrument used in making electrochemical determinations. WO 9429024(A1) describes a sample segment uniquely adapted for automated handling and processing wherein the sample segment may retain selected reagents and a sealing cover is held by ribs, stretched and pressed against raised bosses formed around the well openings to provide a sure seal. The processing steps involved in the preparation of a sample are generally labor-intensive and require expensive reagents. Further, despite being of a disposable nature, the sample segments and cuvettes are quite expensive to manufacture.

U.S. Pat. No. 7,423,750 describes methods and optical systems for scanning of a target sample, including methods and systems using a low mass scan head and methods and systems for conducting a scanned optically transduced assay where the scanning includes at least one first relative angular motion and at least one second angular motion or at least one linear motion. U.S. Pat. No. 6,827,901 discloses an automated immunostaining apparatus having a reagent application zone and a reagent supply zone. The apparatus has a carousel slide support supporting a plurality of slide supports thereon, and drive means engaging the carousel slide support for consecutively positioning each of a plurality of slide supports in the reagent application zone. The methods and devices are not adaptable for a variety of different assays and measurement systems, and are generally useful for only one particular kind of measurement. Further, the components used, especially the disposable ones, are quite expensive requiring accurate and precise machining to reduce the imperfections to a minimum.

Hence, there is a dire need in the art to provide a sample to a fluorescent measurement device requiring inexpensive components and little sample preparation methods such that a variety of different measurements may be conducted in a scant-resource, harsh environments.

SUMMARY OF THE INVENTION

In one embodiment of the invention, the invention provides a sample assembly for a measurement device. In one embodiment, the sample assembly comprises at least one sample carrier. The sample assembly also comprises a sample holder to hold the at least one sample carrier in place. The sample assembly may further comprise a movable platform, such as a spin chuck.

In another embodiment of the invention, the invention provides different devices that each comprise the sample assembly of the invention.

In another embodiment, a sample assembly comprises a sample presentation apparatus. The sample presentation apparatus comprises a sample carrier slide holder, a round sample support and at least one sample carrier slide. In one embodiment, the round support has flange region and a central gear region elevated with respect to the flange region and having spaced apart pairs of indexing gear cogs disposed on the edge of the flange region at an intermediate radius locations of the support for aligning the sample carrier slide holder and sample carrier slides.

A superior method of manufacturing the round support includes machining the round support. The central elevated gear region is preferably machined on a plate or other component to make a single unitary piece round support. In this manner, the indexing gear cogs are already aligned during manufacture of the single unitary piece. In one example, CNC machining is used.

The sample carrier slide holder is removably supported on the round support and has a central hub with at least one arm extending radially from the sample carrier slider holder with each arm being aligned between one pair of indexing gear cogs. In one example, there is a plurality of arms extending radially from the center of the sample carrier slide holder. The arms may be equally spaced apart. The arms may include a detent mechanism for releasably securing the sample carrier slide to the support plate at each arm.

Each of the sample carrier slides are removably supported on the support plate and aligned by one pair of indexing gear cogs. A front end of each sample carrier slide has two indentations each sized and spaced to receive an indexing gear cog of one pair of cogs to achieve alignment of each sample carrier. The sample carrier slide includes a U-shaped channel with wells or ports on each side through which the sample is introduced. The channels and wells may hold biological samples or other desired samples to be scanned by an optical assembly. Where the sample carrier slide comprises a U-shaped channel, the channel may be aligned with a circumferential periphery of the round support. Each sample carrier slide may include a radially outward finger grip for ease in loading onto and removal of the sample carrier slide from the optical assembly.

In one embodiment, the round support includes means for fastening to the movable platform including, in one example, a spin chuck. The round support plate has a corresponding hole for an indexing pin on an upper surface of a spin chuck. An underside of the round support has a first array of magnets that are opposed and slightly offset relative to a second array of magnets on the upper surface of the spin chuck. Coarse alignment of the round support relative to the spin chuck is achieved when the indexing pin is received within the corresponding hole and fine alignment is achieved when the attraction between the first array of magnets and the second array of magnets causes movement of the indexing pin to a fixed biased position within the hole and slight rotation of the round support relative to the movable platform.

In another embodiment, a plurality of pairs of indexing pins is disposed at intermediate radius locations of the round support for alignment of the sample carrier slide holder and sample carrier slides. Each arm of the sample carrier slide holder is aligned between one pair of indexing pins. Each sample carrier slide includes indentions at a top portion which received sample carrier pins for alignment of the sample carrier slides.

In one embodiment, the optical assembly includes an arrangement of a rotary stepper motor and a linear stepper motor for rotating and/or moving linearly the sample assembly so as to be scanned by the optical detection and measurement device. A spin chuck disposed on top of the rotary stepper motor is connected to the arrangement of motors and to the sample assembly or sample presentation apparatus. As the spin chuck is rotated and/or moved linearly, so is the sample assembly or sample presentation apparatus.

BRIEF DESCRIPTION OF THE FIGURES

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

As used herein and in the claims, the singular forms "a," "an," and "the" include the plural reference unless the context clearly indicates otherwise.

Figure 1:
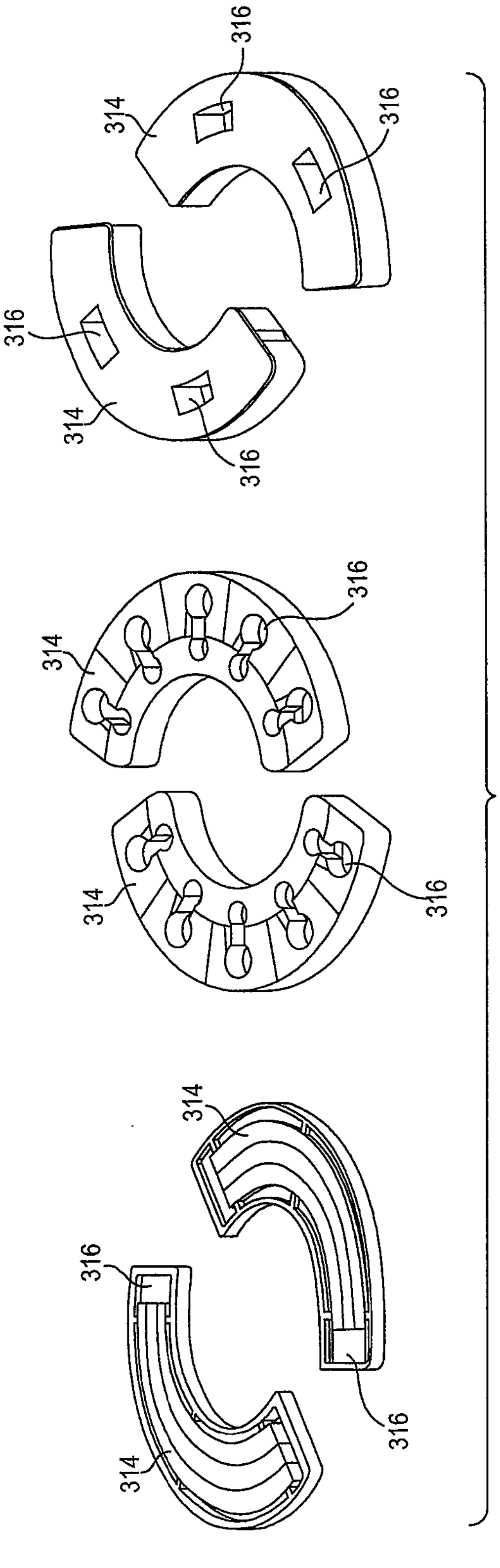
FIG. 1 shows some exemplary sample carriers of the invention.

In one embodiment, the invention provides a sample assembly. The sample assembly is used to provide a sample for analysis by a fluorescence measurement device. In one embodiment, the sample assembly comprises at least one sample carrier. The sample carrier may be any one of a cuvette, channel, well, capillary, membrane, bead and combinations thereof. FIG. 1 shows some exemplary sample carriers 314 shaped in the form of a crescent. One skilled in the art would perceive that the shape of the sample carrier could be anything as long as it can be fit properly into the sample assembly. The sample carrier has a predefined sample region to receive the sample, depicted in FIG. 1 by the numeral 316. In one embodiment, the predefined sample region 316 has a thickness that ranges from about 5 micrometers to about 500 micrometers.

In another embodiment, the predefined sample region 316 of the sample carrier 314 to receive the sample has a thickness that ranges from about 50 micrometers to about 150 micrometers. Sample assembly may comprise a plurality of sample carriers, wherein all the sample carriers comprise a sample or only a few sample carriers comprise sample while the remaining are empty during operation of the device of the invention. Sample may be prepared in situ in the sample carrier or it may be prepared separately and then added into the sample carrier. In situ preparation of sample would involve having a fluorophore-containing reagent as part of the sample carrier. Adding a prepared sample into the sample carrier may be achieved by known means, such as for example pipetting. Additional steps may be required to prepare the sample for measurement, which may include, for example, mixing, vortexing, heating, incubating, and the like. Thus, additional equipment may also be required for performing such additional steps. The nature of the sample carrier may be specific for a particular application, the choice of which will be obvious to one of ordinary skill in the art. In one exemplary embodiment, the sample carrier is a cuvette, and in another exemplary embodiment, the sample carrier is a capillary.

In some instances, the sample is introduced into the sample carrier from a port, following which, the sample is allowed to flow along a predefined path. Such a situation may be in effect when, for example, sample carrier is a capillary. Other forms of sample carriers may also include predefined flow paths. In such instances, at least one portion which is transparent from at least one side. The transparent portion will allow light to pass through to perform measurements for assays.

Figure 2B:
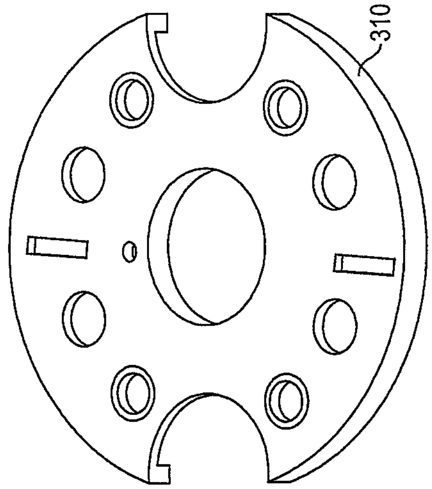
FIG. 2*b* shows the bottom side of an exemplary sample holder of the invention.
Figure 2A:
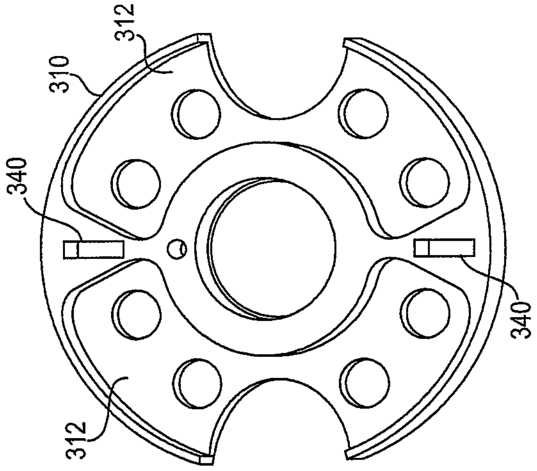
FIG. 2*a* shows the top side of an exemplary sample holder of the invention.

The sample assembly of the invention then comprises, in one embodiment, a sample holder comprising at least one receptacle to receive the at least one sample carrier. FIG. 2*a* shows the top side of the sample holder 310 and FIG. 2*b* shows the bottom side of the sample holder 310. The sample holder 310 comprises at least one receptacle 312 to receive the sample carrier 314. The receptacle 312 is shaped in such a way to receive and hold the sample carrier 314 such that the sample carrier 314 fits snugly without shaking or moving during measurement. The at least one receptacle 312 may also comprise means of securing the sample carrier 314 onto the sample holder 310. Such means of securing are known in the art, and may include, for example, fasteners, screws, bolts, magnetic means, and the like. The receptacle 312 may be shaped to take a single unique sample carrier 314, or it may be fabricated in such a manner that it can take a variety of different types of sample carriers 314. In some embodiments, the sample holder 310 may further comprise at least one predefined calibration region 340 to hold some extraneous material for other types of testing, such as a reference compound for calibration or quantitation. In other embodiments, the sample carrier may comprise at least one predefined calibration region to hold the extraneous material. The reference compound is held in the calibration region by appropriate means known to those skilled in the art. In one exemplary embodiment, the reference compound is sealed in the calibration region using a top, which is preferably transparent to light of predefined wavelengths to allow for appropriate measurements.

Figure 3:
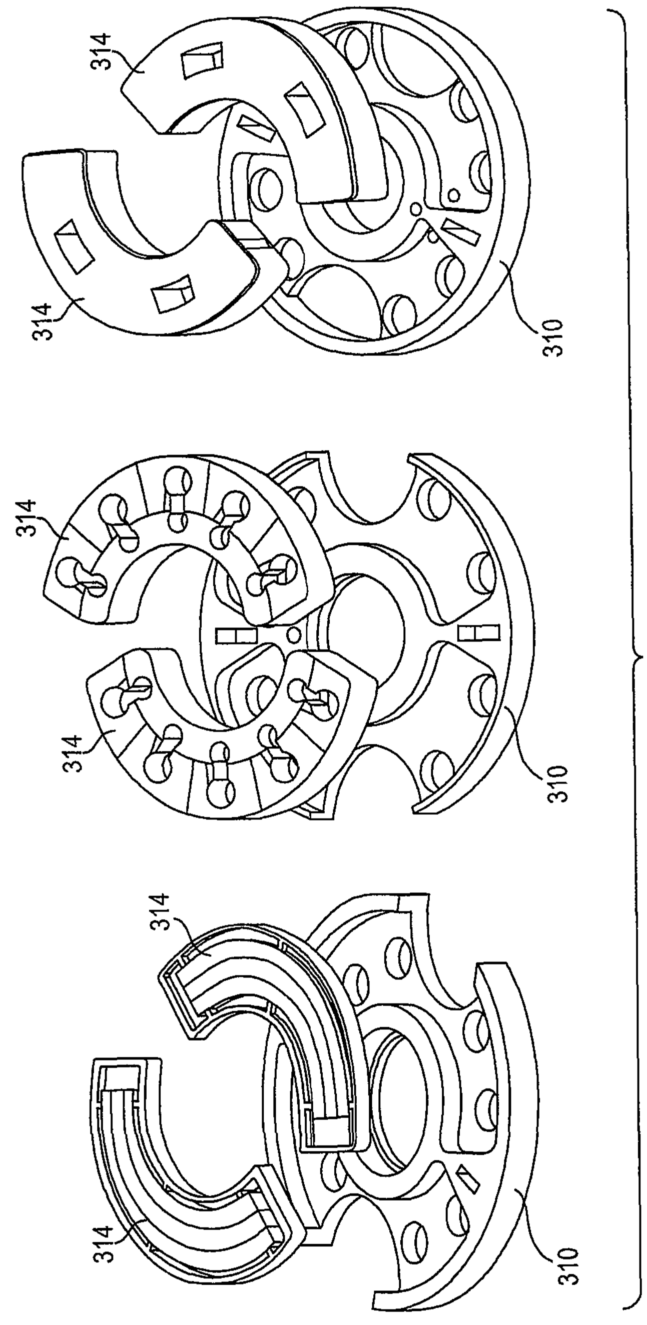
FIG. 3 shows the sample carrier and the sample holder on the verge of being locked together.

FIG. 3 shows a variety of sample carriers 314 on the verge of being secured onto the respective receptacles 312 of a sample holder 310. The sample carrier 314, the receptacle 312 and the sample holder 310 may be fabricated using any suitable material conducive for mass manufacturing, such as, but not limited to, aluminum, titanium, stainless steel, ABS, polyethylene, polypropylene, polystyrene, polyester, polycarbonate, and appropriate combinations thereof. It will also be obvious to one of ordinary skill in the art to fabricate two or more components together and provide them as a single piece. For example, the sample holder 310 and the receptacle 312 may be made available as a single piece to receive the sample carrier 314. Similarly, sample holder 310, receptacle 312 and the sample carrier 314 may be made available as a single piece.

Figure 4:
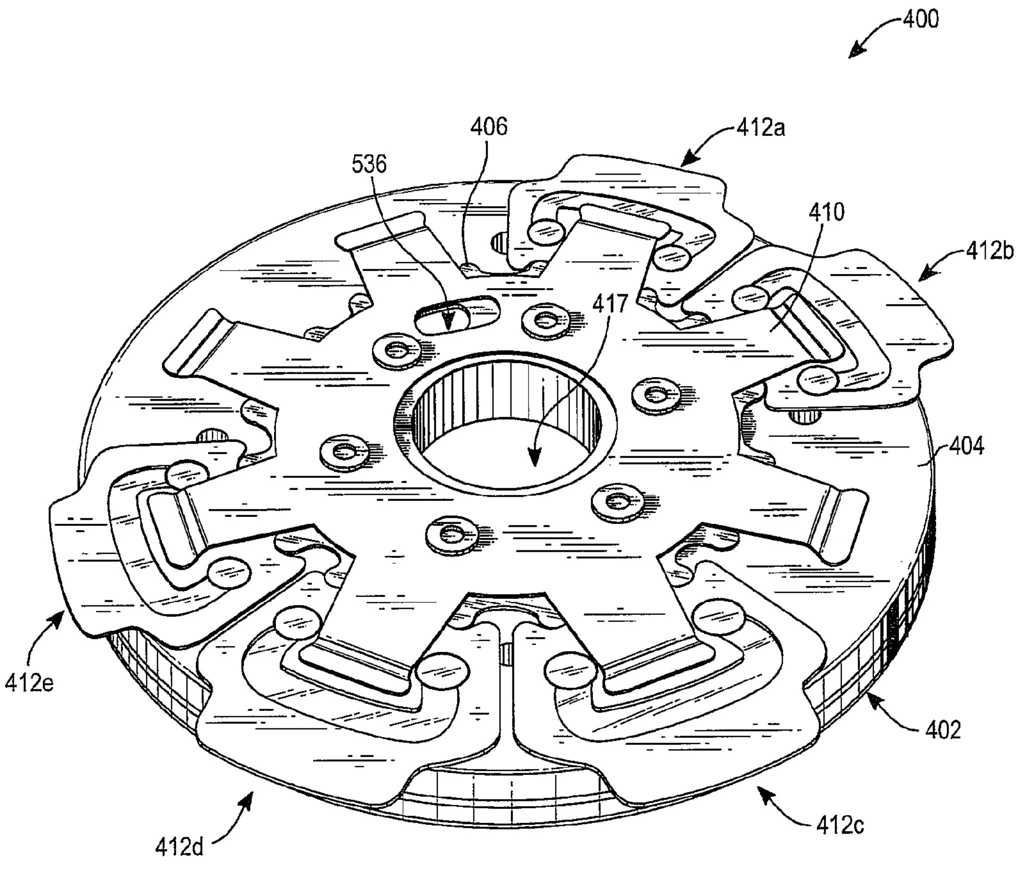
FIG. 4 shows a perspective view of a sample presentation apparatus.
Figure 5:
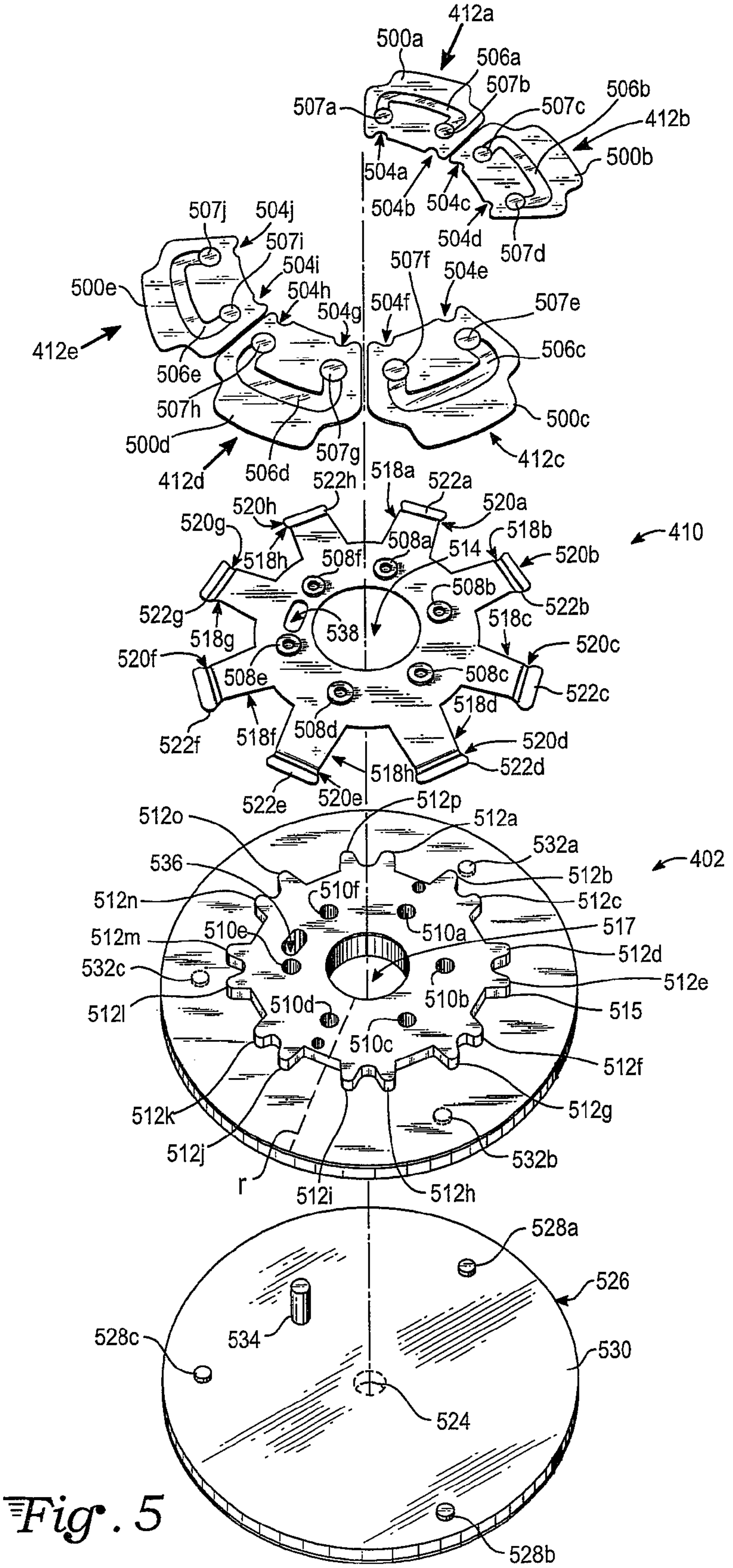
FIG. 5 shows an exploded view of the sample presentation apparatus and movable platform of FIG. 4.
Figure 6:
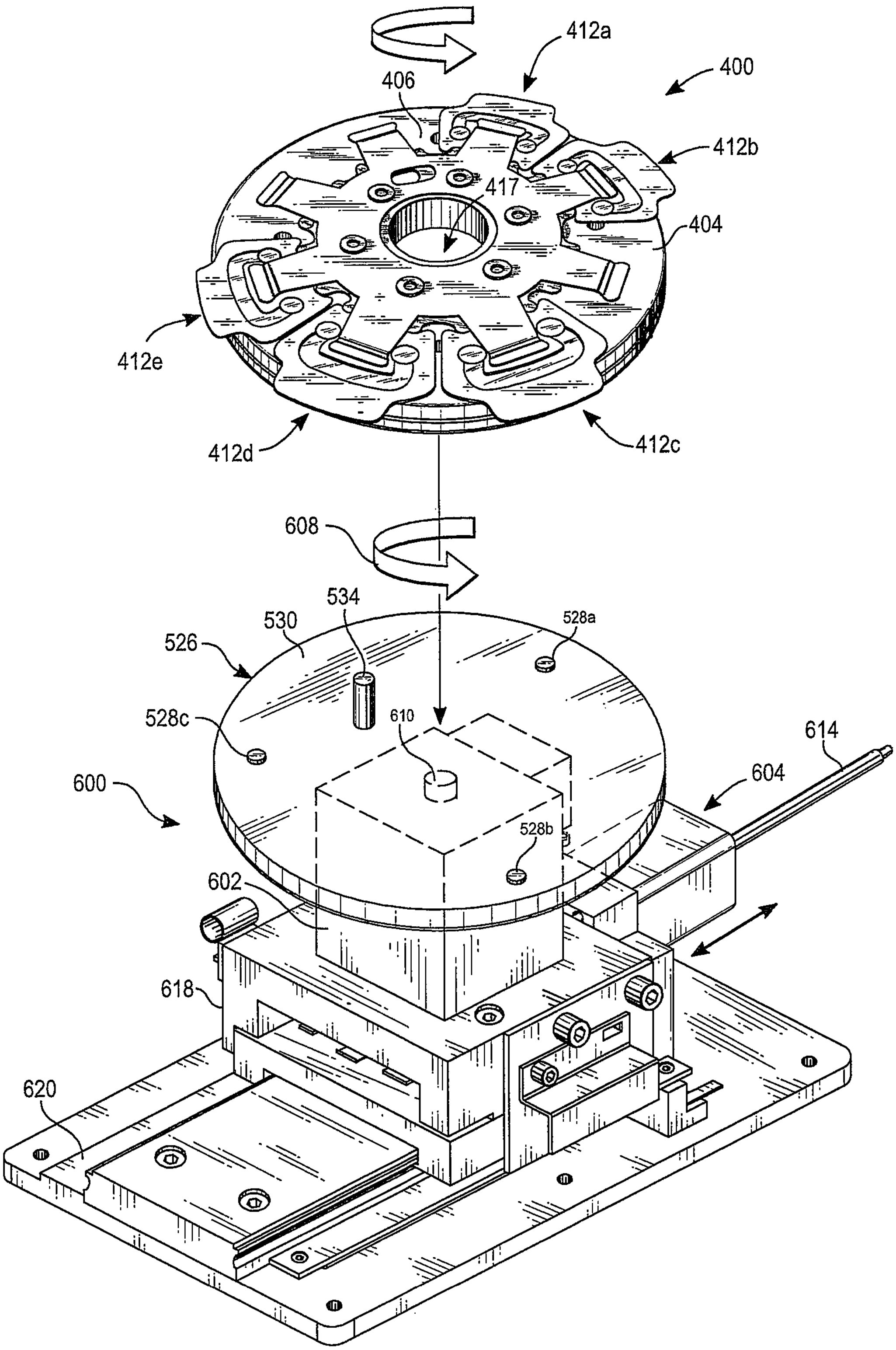
FIG. 6 shows an arrangement of the rotary and linear stepper motors for moving the sample presentation apparatus of FIG. 4 in linear and arcuate trajectories.

In one embodiment, the sample assembly may comprise a sample presentation apparatus 400 as seen in FIGS. 4, 5 and 6. The sample presentation apparatus includes a support, such as a round support 402, with a flange region 404 and a gear region 406 elevated with respect to the flange region. The round support may or may not include opening 417. The gear region 406 has at an outer edge 515 a plurality of pairs of indexing gear cogs 512*a,b*; 512*c,d*; 512*e,f*; 512*g,h*; 512*i,j*; 512*k,l*; 512*m,n*; and 512*o,p* for aligning a sample carrier slide holder 410 and sample carrier slides 412, for example slides 412*a-e*. Each indexing gear cog is disposed at an intermediate location of radius r of the support 402. In a preferred embodiment, a single piece support 402 having the elevated gear region 406 including the plurality of pairs of indexing gear cogs and the flange region 404 is created by machining a starting plate or other starting component. Machining is advantageous for at least the reason that the indexing gear cogs 512*a-p* are precisely positioned by using a relatively inexpensive and simple machining method. In one example, a CNC machine tool is used to make the support having the elevated gear region 406 and flange region 404.

The sample carrier slide holder 410 is removably fastened to and supported on the round support 402 and has a hub or center in vertical alignment with the center of the round support. The sample carrier slide holder has an opening 514 in the center in vertical alignment with opening 517, if present, to form hole 417. Sample carrier slide holder 410 has at least one arm 518, and preferably a plurality of arms 518*a-h*, extending radially from the center 514 of sample carrier slider holder 410.

Each arm 518*a-h* is alignable between one different pair of indexing gear cogs 508*a-p*. Each pair of indexing gear cogs may be equally spaced apart from each adjacent pair and cogs within pairs may be equally spaced apart. Each arm 518*a-h* may be equally spaced from each adjacent arm.

Each arm 518*a-h* may include one detent mechanism 520*a-h* for releasably securing one sample carrier slide 412 to the support 402 at each arm. The detent mechanism 520*a-h* of each arm 518*a-h* may comprise one step 522*a-h* at an end of each arm 518*a-h* which is forced upwardly when a sample carrier slide 412 is moved underneath it to be retained and when sample carrier slide 412 is removed from it to be removed. Only sample carrier slides 412*a-e* are shown but there may be as many sample carrier slides as there are arms 518 or less than the number of arms. Another type of detent mechanism may be used.

Each of the sample carrier slides 412*a-e* is removably supported on the support 402 and aligned by a respective pair of indexing gear cogs 508. Each sample carrier slide may include one radially outward finger grip 500*a-e* for ease in loading and removal of the sample carrier slides 412*a-e* from the assembly. One front end of each sample carrier slide 412*a-e* has a pair of indentations 504. Indentations 504*a,b*; 504*c,d*; 504*e,f*; 504*g,h*; and 504*i,j* are sized and spaced to receive a pair of indexing gear cogs 508*a,b*; 508*c,d*; 508*g,h*; 508*i,j*; and 508*k,l*, respectively of cogs 508*a-o* to achieve alignment of each sample carrier slide 412*a-e*. For example, sample carrier slide 412*a*, having indentations 504*a,b* receiving indexing gear cogs 512*a,b*, is releasably secured on the support 402 by detent mechanism 520*a* of arm 518*a* which is aligned in between indexing gear cogs 512*a,b*. In one example, the indentations are curved to receive a curved pair of indexing gear cogs. Where the sample carrier slides 412*a-e* each comprise a U-shaped channel 506*a-e*, such as a sample capillary, the channel may be aligned with a circumferential periphery of the round support 402. Each channel 506*a-e* may include wells or ports 507*a-j* at ends of the channels into which sample may be introduced to the channels.

Other embodiments of indexing gear cog arrangements may be used. For example, a different number of pairs of gear cogs may be used. Further, varying sizes of indexing gear cogs may be used. Indexing gear cogs within a pair of gear cogs may be of the same or different size.

The sample carrier slide holder 410 may further be secured to the round support 402 with means of securing known in the art, and may include, for example, fasteners such as screws, bolts, magnetic means, and the like. For example, screws of the sample carrier slide holder seen in FIG. 5 are threaded into corresponding openings 510*a-f* on the support 402 for fastening the sample carrier slide holder to the support.

Referring to FIG. 6, in one embodiment, the optical assembly includes an arrangement of motors 600 including a rotary motor 602 and a linear motor 604 for rotating and/or moving linearly the sample assembly or sample presentation apparatus 400 on a movable platform, such as a spin chuck 526, so as to be scanned by the optical assembly. The movable platform 526 is capable of being moved in a suitable trajectory. The movement may be achieved by the use of a stepper motor, the mechanism of which is known in the art. The movable platform 526 is capable of being moved in a linear trajectory or direction, an arcuate trajectory or direction, or both. In one embodiment, the movable platform 526 is capable of being moved in both a linear and an arcuate trajectory or direction sequentially and/or or simultaneously.

FIG. 6 shows a typical use scenario where a sample assembly, in this example, the sample presentation apparatus 400, is connected to the movable platform 526 and the movable platform is connected to the rotary motor 602 and linear motor 604 for movement. The movable platform 526 is configured in such a way that it can be connected to the sample assembly or presentation apparatus 400 for movement of the sample assembly or sample presentation apparatus. In the example seen in FIGS. 5 and 6, the movable platform 526 is a spin chuck.

FIG. 6 shows the sample presentation apparatus 400 securable to the movable platform 526. The spin chuck 526 is connected to the rotary motor 602, for example rotary stepper motor or other spinner, to achieve movement of the spin chuck 526 in an arcuate trajectory or direction as shown by reference numeral 608. For example, rotating shaft 610 is received within a hole 524 (FIG. 5) in the spin chuck 526 to impart the rotational movement to the spin chuck. When the rotary stepper motor 602 rotates, the connected spin chuck 526 rotates and the sample presentation apparatus 400 or sample assembly rotates with the spin chuck and rotary stepper motor 602. The spin chuck is connected to stepper motor 604, for example linear stepper motor, which has an arm 614 for linear movement of the spin chuck 526 in a linear trajectory or direction as shown by reference numeral 616. The rotary stepper motor 602 is connected to a carriage 618 which is provided with linear movement by linear stepper motor 604. The carriage 618 moves linearly along a track 620 thereby causing the connected rotary stepper motor 602, spin chuck 526 and sample presentation apparatus 400 to move linearly with the carriage 618.

With reference to FIG. 6, the movable platform 526 is attached to the support 402 or a sample carrier holder through a suitable locking means. Locking means are known to those of ordinary skill in the art, and may include fasteners, mechanical means, magnetic means, and the like. In one embodiment, the locking means is by magnetic means. In one example, a magnetic material is present on at least one portion of the support 402 or sample holder, and a magnetic material of the opposite polarity and suitable magnetic strength is made available at the complementary position of the movable platform 526. This will ensure that when the two components are brought together, they will be held strongly in place through magnetic attraction forces. In another embodiment, the locking means is through mechanical means. This includes means such as using screws, bolts, and the like.

In one example, a self-alignment mechanism for the support 402 or sample holder comprises the following means. In FIGS. 5 and 6, three magnets 528*a-c* are disposed on an upper surface 530 of the movable platform 526 and three magnets 532*a-c* of the same size and opposite polarity are disposed in an opposing slightly offset vertical alignment position on an underside of the round support 402 (FIG. 5). In one embodiment, adjacent magnets 528*a-c* on the movable platform are spaced apart at equal intervals and adjacent magnets 532*a-c* on the support are spaced apart at equal intervals. At least one indexing pin 534 on the upper surface 530 of the movable platform is received by corresponding hole 536 extending through the round support in a complementary position on the round support 402 through which the indexing pin 534 may pass. Sample carrier slide holder 410 may have a hole 538 which when in vertical alignment with the round support becomes a part of the hole 536. Opposed attracting magnets on the movable platform 606 and support 402 or sampler holder are slightly offset so that after course alignment of the support and movable platform is achieved by entry of the indexing pin 534 of the movable platform into the corresponding hole 536. Fine alignment between the round support and the spin chuck then occurs because the attraction between the opposed magnets 528*a-c* and 532*a-c* cause slight rotation of the movable platform 525 and support 402 (or sample holder), similar to bayonet rotation, pushing the indexing pin 534 to a fixed, biased position within its corresponding hole 536 removing any play that may exist within the hole or holes. In another example, not shown, the sample carrier 314 is loaded onto the sample holder 310, which is in turn loaded onto and attached to the movable platform 526 in a similar manner.

All the components lock into place to form a single unit. Then, when the movable platform 526 moves, the entire sample presentation apparatus 400 or sample assembly moves. In one embodiment, the movable platform 526 may comprise a part of the sample presentation apparatus or sample assembly or may be separate from it.

Figure 7:
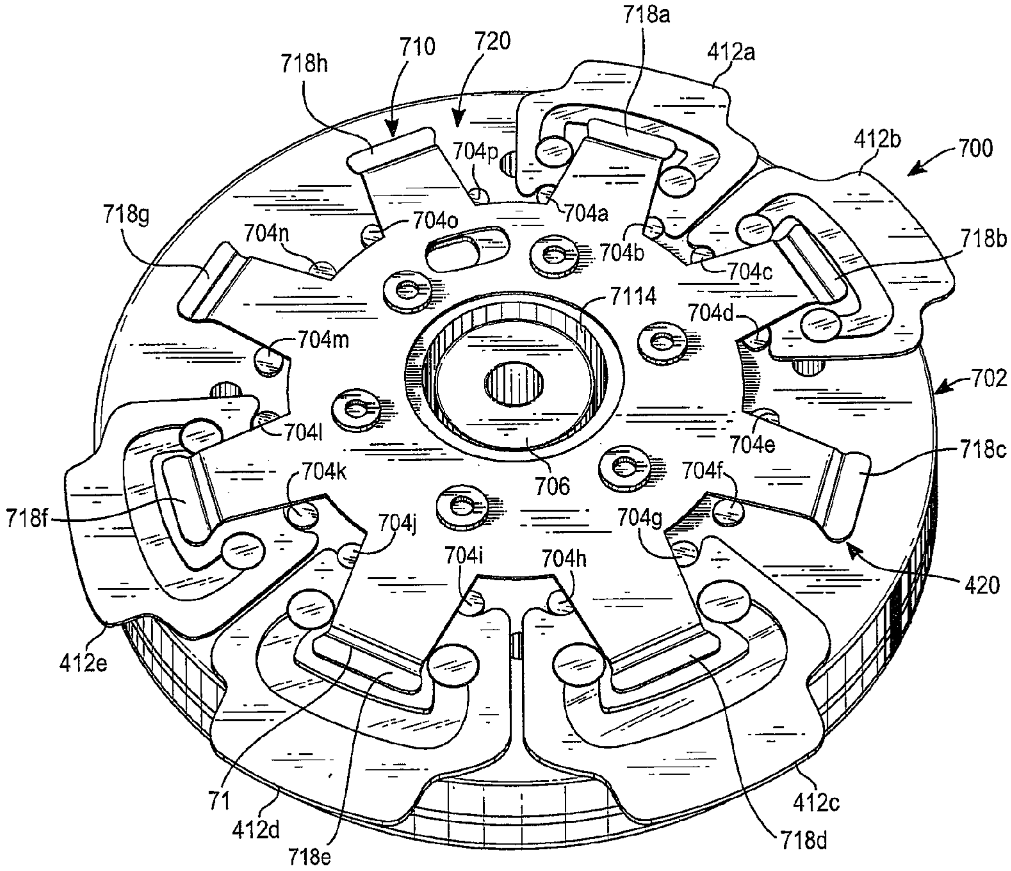
FIG. 7 shows an alternative embodiment of a sample presentation apparatus.

In one embodiment, as seen in FIG. 7, the sample assembly may comprise a presentation apparatus 700 which includes a support, such as a round support 702, with spaced apart pairs of projections, for example pairs 704*a,b*; 704*c,d*; 704*e,f*; 704*g,h*; 704*i,j*; 704*k,l*; 704*m,n*; and 704*o,p*, disposed at an intermediate radius location of the support for support and alignment of a sample carrier slide holder 710 and sample carrier slides, for example 412*a-e*. The sample carrier slide holder is removably supported on the round support and has a hub 714 or center with at least one arm 718*a-h* extending radially from the sample carrier slider holder and each arm being aligned between a first pair of projecting pins. In one example, there is a plurality of arms extending radially from the center of the sample carrier slide holder, each of the arms being aligned between a different pair of projecting pins. Each pair of pins may be equally spaced apart from adjacent pair of pins and pins within pairs of pins may be spaced apart equally. Each arm of the sample carrier slide holder may be equally spaced from each adjacent arm. Each sample carrier slide includes a pair of indentations on a front end sized and spaced to receive one pair of projection pins to align the carrier slide on the support. A detent mechanism 720 is used to secure the sample carrier slides on the support. Round support 702 may include a central projection 706 for insertion within an opening of sample carrier slide holder 710.

When an incident beam is allowed to impinge on the sample, the movement of the sample assembly or sample presentation apparatus causes different portions of the sample to be illuminated by the incident beam, giving rise to space-dependent fluorescence signals. It will also be obvious to one of ordinary skill in the art that the entire sample assembly or sample presentation apparatus may be manufactured as a single unit, or as individual components. It is also important that the individual components, namely the sample carrier, the sample holder and/or the movable platform or the sample presentation apparatus are secured so that—when the movable platform is moving in a suitable trajectory, there is no wobble or shake of the sample carrier within the receptacle or sample carrier slide, or spilling of sample from the sample carrier or sample carrier slide.

The stepper motor used to control the movable platform may be a combination of linear stage stepper motor and a rotary stepper motor. Other kinds of stepper motors, such as, a focus stage stepper motor may also be made available for the sample assembly or sample presentation apparatus of the invention. The stepper motors may be controlled using a field programmable gate array (FPGA). The rotary stepper motor can be arranged to rotate the sample assembly at a constant rotational speed. The linear stage stepper motor can be arranged to continuously move the rotating sample assembly linearly during measurement. The focus stage stepper motor can be arranged to move a focusing lens up or down to a particular position (similar to a microscope) before a scanning sequence is started, and to then hold that lens position during the scanning sequence to ensure better focus of laser spot onto the sample.

In one exemplary embodiment, the rotary stage stepper motor can be a 50-pole stepper having 4 windings. The rotary stage stepper motor can be designed to rotate the sample assembly or sample presentation apparatus at a relatively low speed, such as, for example, 10 rpm, while providing a high level of repeatability between adjacent scans. Such a low-speed is preferable to prevent encountering problems with regard to signal-to-noise ratios. In a typical stepper motor, discrete signals are directed to a driver, resulting in the stepped motion. To prevent such a stepped motion, a look-up table can be provided for the rotary stage stepper motor which is used to direct current values to the poles of the motor so that the rotary stage stepper motor sees a uniform magnetic field resulting in the continuous rotary motion without any stepping.

According to the present teachings, an integrated, protected dual H-bridge with external components and logic can be implemented to regulate the current precisely to the stepper motors. In the design of the present teachings, no heat-sinking or active cooling is required at the expected ambient conditions and with loads of less than 1 A peak per coil. More particularly, the look-up table of the FPGA can be connected to power drivers which operate to amplify the current values after they have been converted from digital to analog signals in the digital-to-analog converters. Since there are multiple windings going into the motor, each winding can be provided with a power driver.

An encoder can be connected to the rotary stage stepper motor. By using position data from the encoder, or the frequency of the encoder signal, the angular position of the rotary motor may be tracked to ensure that the rotary motor is rotating at a constant velocity. In addition, the encoder position can also be used to monitor the motor position during starting and stopping conditions.

The focus stage stepper motor can also be controlled through a look-up table. The focus stage stepper motor can operate to adjust the focusing lens when conducting a scan to compensate for fabrication imperfections in the sample holders and/or sample carriers or other components, to compensate for any misalignment, tilt, and/or wobble in the sample assembly or sample presentation apparatus, and any other inevitable misalignments.

The linear stage stepper motor and the focus stage stepper motor can also be controlled by photointerrupters. One photointerrupter can be arranged for a home position on each of the linear and focus stages, and one for the sample carrier or sample carrier slide holder and support loading stage. This will ensure that the sample assembly does not run past an end point and result in erroneous and/or inaccurate results, or sometimes even complete breakdown of the sample assembly.

The sample assembly of the invention provides for inexpensive alternative to existing sample assemblies, in that the manufacturing methods need not be too intricate so that individual components of the sample assembly can be fabricated with some level of imperfections. The construction and use of the sample assembly or sample presentation apparatus in a suitable measurement device accounts for all the imperfections. This allows for reducing the cost of the sample assembly or sample presentation apparatus, and hence the entire device comprising it. Further, this also allows for point-of-care measurement devices in remote locations, especially in situations where regular resources are scant and the environment is typically harsh for operation of any other device.

Thus, in another aspect, the invention provides a device that comprises the sample assembly or sample presentation apparatus of the invention. The device useful in the invention is a fluorescent measurement device. Such a fluorescent measurement device may be used for a variety of applications, that include for example, assays such as immunoassays, sandwich immunoassays, competitive immunoassays, other diagnostic applications, and the like. Other exemplary applications may include measuring water purity, identifying presence of narcotics, and so on.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A sample presentation apparatus for an optical detection and measurement device, comprising:

a round movable support having a flange region and a central gear shaped region elevated with respect to the flange region, with a plurality of pairs of indexing gear cogs on an outer edge of the gear shaped region;

a spin chuck carrying the round movable support;

a rotary stepper motor connected to the spin chuck so as to drive the spin chuck with rotary motion;

a sample carrier slide holder removably supported on and co-axial and movable with the round movable support, having a plurality of arms extending radially from a central hub of the sample carrier slide holder, each arm being aligned between a different pair of indexing gear cogs; and at least one sample carrier slide removably supported directly on the round movable support and aligned by a pair of indentations in each slide being received by a corresponding pair of indexing gear cogs, the carrier slide having a channel that is U-shaped in an orientation whereby the U-shaped channel is aligned with the circumferential periphery of the round movable support.

2. The sample presentation apparatus of claim 1, wherein the round movable support and elevated gear shaped region comprise a unitary piece.

3. The sample presentation apparatus of claim 1, wherein a front end of each sample carrier slide has two indentations, each indentation sized and spaced to receive an indexing gear cog of one pair of indexing gear cogs to achieve alignment of each sample carrier slide.

4. The sample presentation apparatus of claim 1, wherein each pair of indexing gear cogs is spaced an equal amount from an adjacent pair of indexing cogs and a space between indexing cogs of each pair of indexing cogs is equal.

5. The sample presentation apparatus of claim 1, wherein the plurality of spaced arms extending radially from the sample carrier slide holder are equally spaced from each other.

6. The sample presentation apparatus of claim 1, wherein each arm includes a radially outward finger grip.

7. The sample presentation apparatus of claim 1, wherein each arm comprises a detent mechanism for releasably securing the sample carrier slide to the round movable support at each arm.

8. The sample presentation apparatus of claim 1, wherein the round movable support and the sample carrier slide holder include openings in vertical alignment with each other and in vertical alignment with an indexing pin of the spin chuck.

* * * * *